(12) United States Patent
Guenschel et al.

(10) Patent No.: US 7,832,254 B2
(45) Date of Patent: Nov. 16, 2010

(54) PARTICULATE SENSOR AND METHOD FOR OPERATING A PARTICULATE SENSOR

(75) Inventors: Harald Guenschel, Gerach (DE); Uwe Glanz, Asperg (DE); Stefan Zimmermann, Pfinztal (DE); Leonore Schwegler, Stuttgart (DE); Juergen Sindel, Vaihingen/Enz (DE)

(73) Assignee: Robert Bosch GmbH, Stuttgart (DE)

( * ) Notice: Subject to any disclaimer, the term of this patent is extended or adjusted under 35 U.S.C. 154(b) by 57 days.

(21) Appl. No.: 11/664,238

(22) PCT Filed: Sep. 9, 2005

(86) PCT No.: PCT/EP2005/054475

§ 371 (c)(1),
(2), (4) Date: Dec. 14, 2007

(87) PCT Pub. No.: WO2006/034951

PCT Pub. Date: Apr. 6, 2006

(65) Prior Publication Data

US 2008/0202943 A1    Aug. 28, 2008

(30) Foreign Application Priority Data

Sep. 30, 2004   (DE)   ........................ 10 2004 047 465
Apr. 1, 2005    (DE)   ........................ 10 2005 015 103

(51) Int. Cl.
*G01N 37/00* (2006.01)
(52) U.S. Cl. .................................................. 73/28.01
(58) Field of Classification Search ................. 73/28.01
See application file for complete search history.

(56) References Cited

U.S. PATENT DOCUMENTS

| 4,307,061 A | 12/1981 | Sarholz et al. |
| 2001/0054553 A1 * | 12/2001 | Isomura et al. ............. 204/431 |

FOREIGN PATENT DOCUMENTS

| DE | 42 36 711 | 5/1993 |
| DE | 198 53 841 | 6/1999 |
| DE | 101 28 869 | 1/2002 |
| DE | 102 44 702 | 5/2003 |
| GB | 1 495 699 | 12/1977 |

* cited by examiner

*Primary Examiner*—Hezron Williams
*Assistant Examiner*—Alex Devito
(74) *Attorney, Agent, or Firm*—Kenyon & Kenyon LLP

(57) ABSTRACT

A sensor for determining the concentration of particulates in gas mixtures is described, a soot sensor in particular, having a ceramic sensor body surrounded by a metallic housing and having a first and a second measuring electrode. In this instance, the first measuring electrode is connected to the metallic housing of the sensor or the metallic housing of the sensor is designed as the first measuring electrode. By additional electrodes on the ceramic body, the sensor is operable also as a lambda sensor.

26 Claims, 5 Drawing Sheets

PARTICULATE SENSOR AND METHOD FOR OPERATING A PARTICULATE SENSOR

FIELD OF THE INVENTION

The present invention is directed to a sensor for determining particulates in gas mixtures, in particular a soot sensor, and a method for operating this sensor.

BACKGROUND INFORMATION

As a result of increasingly strict environmental legislation, exhaust gas treatment systems allowing soot particles existing in combustion exhaust gases to be filtered out or eliminated are gaining in importance. In order to check or monitor the functionality of such exhaust gas treatment systems, sensors are needed which allow the instantaneous particulate concentration existing in the combustion exhaust gas to be accurately determined even in extended operation. In addition, sensors of this type should allow the load of diesel particulate filters, for example, provided in an exhaust gas system, to be predicted in order to achieve a high degree of system reliability, thus allowing the use of more cost-effective filter materials.

German Patent document DE 102 44 702 A1 discusses a sensor for detecting substances in a fluid stream which includes two measuring electrodes at a distance from each other which are exposed to the combustion exhaust gas to be examined. One of the electrodes is connected to a high-voltage source, so that a voltage between 1 kV and 10 kV is applied to the electrode.

Dielectrically hindered discharges occur between the measuring electrodes, the current between the measuring electrodes being correlated with the number of particles present in the gas space between the measuring electrodes. The disadvantage of this type of particulate sensor is its relatively complex and therefore cost-intensive design.

An object of the exemplary embodiment and/or exemplary method of the present invention is to provide a sensor for determining the particulate concentration in gas mixtures that exhibits a high degree of accuracy of the measuring signals obtained and yet may be manufactured cost-effectively.

SUMMARY OF THE INVENTION

The sensor and the method having the characteristic features of the independent claims have the advantage that they allow the object of the exemplary embodiment and/or exemplary method of the present invention to be achieved in an advantageous manner. This is based in particular on the simple construction of the sensor and the use of sturdy components which have been advantageously used in ceramic oxygen sensors and spark plugs. The sensor has a metal housing for protection against corrosive exhaust gas components, which, however, allows access to the particles to be determined. A simple construction of the sensor results from the use of the metallic housing as the measuring electrode and as the support of the measuring electrode.

Other advantageous specific embodiments of the present sensor are described herein.

It is thus advantageous if another measuring electrode is at least largely integrated into the ceramic sensor body of the sensor for soot protection. This considerably increases the long-term stability and measuring accuracy of the present sensor.

It is furthermore advantageous if the sensor has an analyzer device which ascertains the number of dielectric discharges per unit of time and outputs this number as a measure of the particulate concentration in the gas mixture.

It is advantageous in particular if the sensor body has a rotationally symmetrical design because in this case the gas mixture has the same possibility of access to the measuring electrodes of the sensor regardless of the positioning of the sensor relative to the flow of the gas mixture.

In a particularly advantageous specific embodiment, the sensor is designed in the form of a spark plug or a lambda sensor, because in this way proven standard components may be used in the manufacture of the sensor. When designed as a lambda sensor, the sensor is advantageously used as a particulate sensor in a first time period and as a lambda sensor in a second time period.

DETAILED DESCRIPTION

Figure 1:
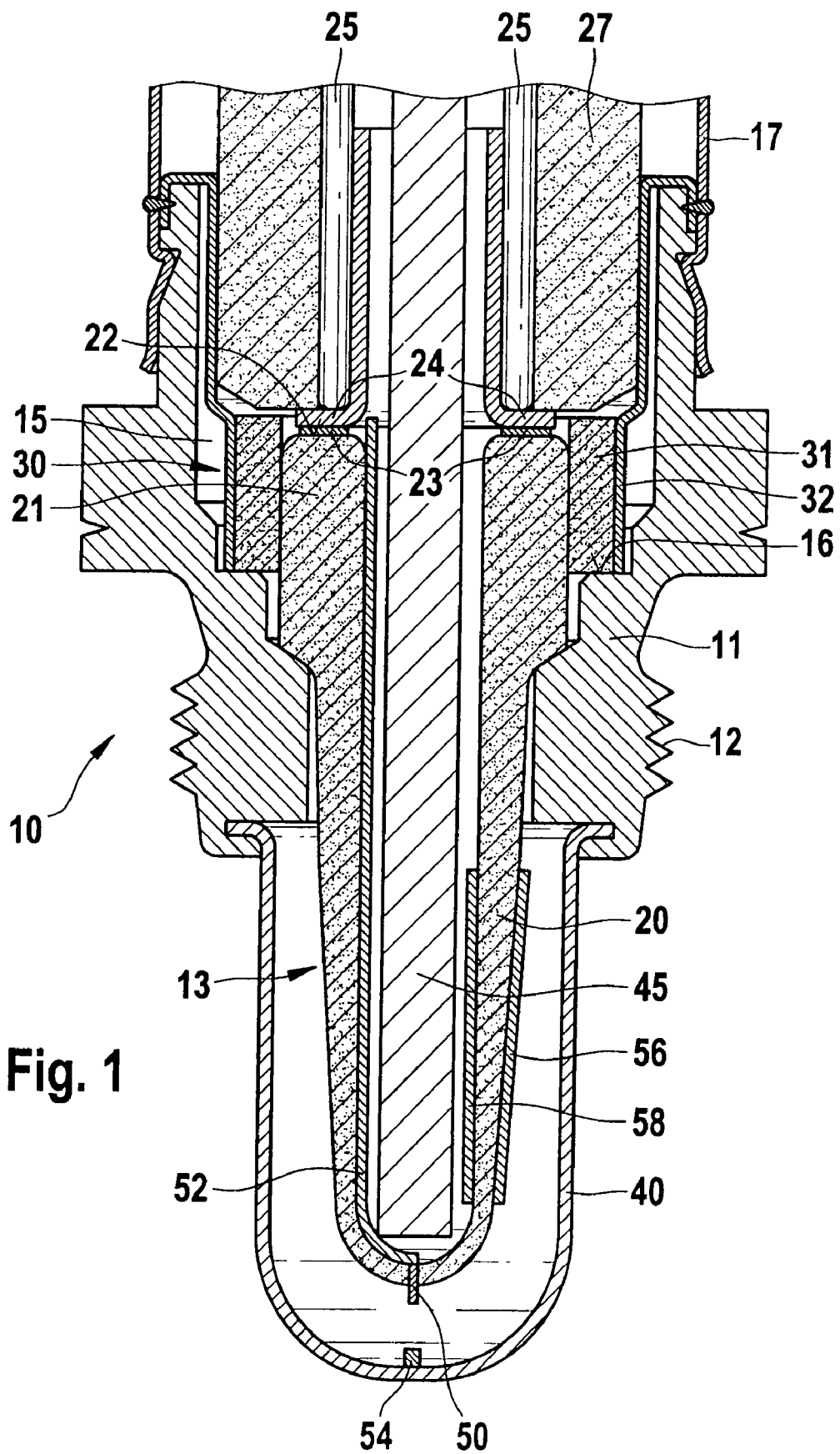
FIG. 1 shows a longitudinal section through a sensor on the basis of components of an oxygen sensor according to a first exemplary embodiment.

FIG. 1 shows a schematic structure of a first specific embodiment of the present invention. Numeral 10 denotes a sensor for determining particulates in a gas mixture surrounding the sensor. Sensor 10 has a metallic housing 11 having a thread 12 as an attachment arrangement for installation in an exhaust pipe (not depicted), and has a sensor ceramic 13, which may have a rotationally symmetrical design. A sealing system 30, which connects sensor ceramic 13 to housing 11 in a gas-tight and electrically insulating manner, is provided between sensor ceramic 13 and housing 11. Sealing system 30 includes a ceramic insulating ring 31 made of an electrically insulating material and a metallic sleeve 32.

Housing 11 has a longitudinal bore 15, which has a stepped design and has an annular surface 16, for example, which supports sensor ceramic 13. The connector side end of housing 11 is surrounded by an encapsulating compound 17, which encloses connector-side components which are not depicted.

Sensor ceramic 13 includes a tubular ceramic body 20, whose measuring gas-side end section is sealed. A bead-shaped head 21 having an annular front face 22 is formed on the connector-side end section of ceramic body 20. Ceramic body 20 may be made of an oxygen ion-conducting solid electrolyte material such as $ZrO_2$ stabilized or partially stabilized with $Y_2O_3$; aluminum oxide additions may also be provided.

Sensor ceramic 13 on the measuring gas side, protruding from longitudinal bore 15, is surrounded by and spaced from a protecting tube 40, which has a plurality of openings (not depicted), situated symmetrically to the central axis of protective tube 40, for example, as inlets and outlets for the gas mixture. Protective tube 40 surrounding the measuring gas-side part of ceramic body 20 may alternatively be designed as a double protecting tube having an outer cylinder sleeve and an inner cylinder sleeve. There is an annular gap between the outer cylinder sleeve and the inner cylinder sleeve. The outer cylinder sleeve has a plurality of gas inlets (not depicted), in particular facing the incoming gas mixture and which may be distributed axially or radially. The inner cylinder sleeve also has a plurality of radially and/or axially distributed inner gas inlets. This system allows the gas mixture to access the sensitive area of sensor 10 while avoiding a turbulent flow of the gas mixture in the immediate surroundings of ceramic body 20.

A rod-shaped heating element 45, for example, is introduced into the inner space of sensor ceramic 13, the heating element being used for at least temporarily heating sensor 10 to a temperature of 600° C. to 700° C., for example, at which the soot deposited on the surface of ceramic body 20 is possibly burnt off. An electrical resistor (not depicted) is integrated into ceramic heating element 45. A resistive printed conductor made of a cermet material may be used as the electrical resistor. This may be a mixture of a metal such as platinum with ceramic components such as aluminum oxide. The resistive printed conductor may be in the form of a meander and has electrical terminals (not depicted) at both ends. By applying an appropriate heating voltage to the terminals of the resistive printed conductor, the heating power of heating element 45 may be appropriately regulated.

A barium-containing aluminum oxide may be used as the ceramic material for electrical insulation of heating element 45 because an insulation of this type has a largely constant high electrical resistance over a long period of time.

On the outside of ceramic body 20, exposed to the gas mixture, a first measuring electrode 50, which may be made of a corrosion-resistant material such as a platinum cermet, for example, is provided. A second measuring electrode, which is used as a counterelectrode to first measuring electrode 50, is formed by protecting tube 40. A lead 52 may be applied to the inside of ceramic body 20 for electrical contacting of first measuring electrode 50. Alternatively, lead 52 may be pressed into the ceramic material of ceramic body 20 and sintered therewith, so that lead 52 is covered essentially from all sides by a ceramic material of ceramic body 20. According to another alternative, measuring electrode 50 may be designed as a wire as an extension of lead 52. Protecting tube 40 is also electrically contacted via a lead (not depicted).

During the operation of sensor 10, a high voltage is applied to first measuring electrode 50 and protecting tube 40. In this way, electrical discharges occur between first measuring electrode 50 and protecting tube 40. If soot particles, for example, fly through the discharge path formed between measuring electrode 50 and protecting tube 40, this modifies the sparkover frequency of the electrical discharge. The number of sparkovers occurring per unit of time may be detected by an analyzer device (not depicted) and correlated with a particulate concentration.

To obtain a well-defined discharge path, protecting tube 40 may have, on its surface opposite to measuring electrode 50, a metal lamina 54 in the form of a catch basket for sparkovers.

Sensor 10 may be used not only for determining the concentration of particulates in gas mixtures, but may also be used for determining gaseous components of the gas mixture.

For this purpose, sensor 10 has a second measuring electrode 56 on the large surface of ceramic body 20 facing protecting tube 40. A reference electrode 58, exposed to a reference gas, for example, air, is located on the inside of ceramic body 20, as a counterelectrode to second measuring electrode 56, at a distance from lead 52 and first measuring electrode 50. Second measuring electrode 56 and reference electrode 58 are connected to electrode contacts 23 situated on front face 22 via track conductors (also not depicted in detail). Contact parts 24 which are each contacted by a connecting cable 25 are in contact with electrode contacts 23. Connecting cables 25 exit from encapsulating compound 17 distant from the measuring gas through a sealing part (not depicted) and are connected to the analyzer device or a control unit. A ceramic insulating sleeve 27, which presses against contact parts 24, is furthermore situated in longitudinal bore 15 of housing 11.

Second measuring electrode 56, together with reference electrode 58, forms an electrochemical Nernst cell. It depends on the determination of the potential difference in the form of a measurable electric voltage resulting from the different oxygen contents in the gas mixture and the reference gas atmosphere.

The oxygen content in the gas mixture may be determined alternating with the determination of the particulate concentration in the gas mixture. In a first time period a high voltage is applied to first measuring electrode 50, i.e., to protecting tube 40, and the particulate concentration in the gas mixture is thus determined, and in a second time period the high voltage applied to first measuring electrode 50, i.e., to protecting tube 40, is switched off and the voltage between second measuring electrode 56 and reference electrode 58 is determined. In this way injection of the high voltage applied to first measuring electrode 50, i.e., protecting tube 40, into the measuring signal of the Nernst cell formed by electrodes 56, 58 is prevented.

Figure 2:
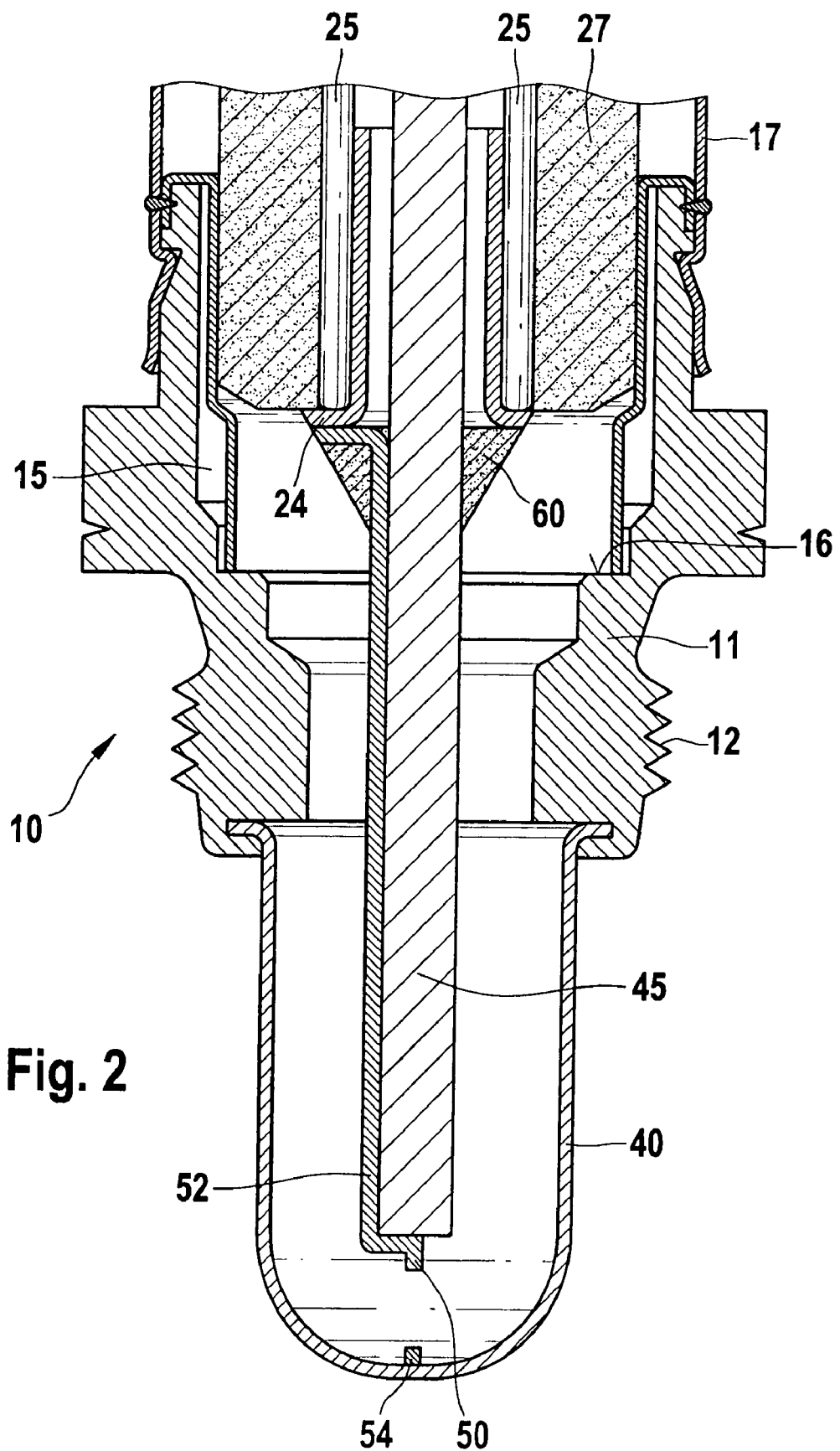
FIG. 2 shows a longitudinal section through a sensor on the basis of components of an oxygen sensor according to a second exemplary embodiment.

FIG. 2 shows a second specific embodiment of a sensor for determining particulates in gas mixtures. The same reference numerals denote the same components as in FIG. 1.

The sensor depicted in FIG. 2 has a design like the one depicted in FIG. 1 and is made of components such as otherwise used in oxygen sensors. In the sensor according to the second exemplary embodiment, a finger-shaped ceramic sensor ceramic 13 is not used. This simplifies the sensor design considerably.

Instead, measuring electrode 50 is positioned on an external surface of heating element 45 and electrically contacted by lead 52. Measuring electrode 50 and lead 52 are applied to heating element 45, which may be by pad pressure or transfer pressure and provided with an aluminum oxide cover (not depicted), for example. Alternatively, lead 52 of measuring electrode 50 may also be integrated into the ceramic material of heating element 45. On the connector side, heating element 45 is sealed to the outside in a gas-tight manner against the gas atmosphere to be determined, which may be by a ceramic seal 60 in the form of a packing made of steatite powder.

Figure 3:
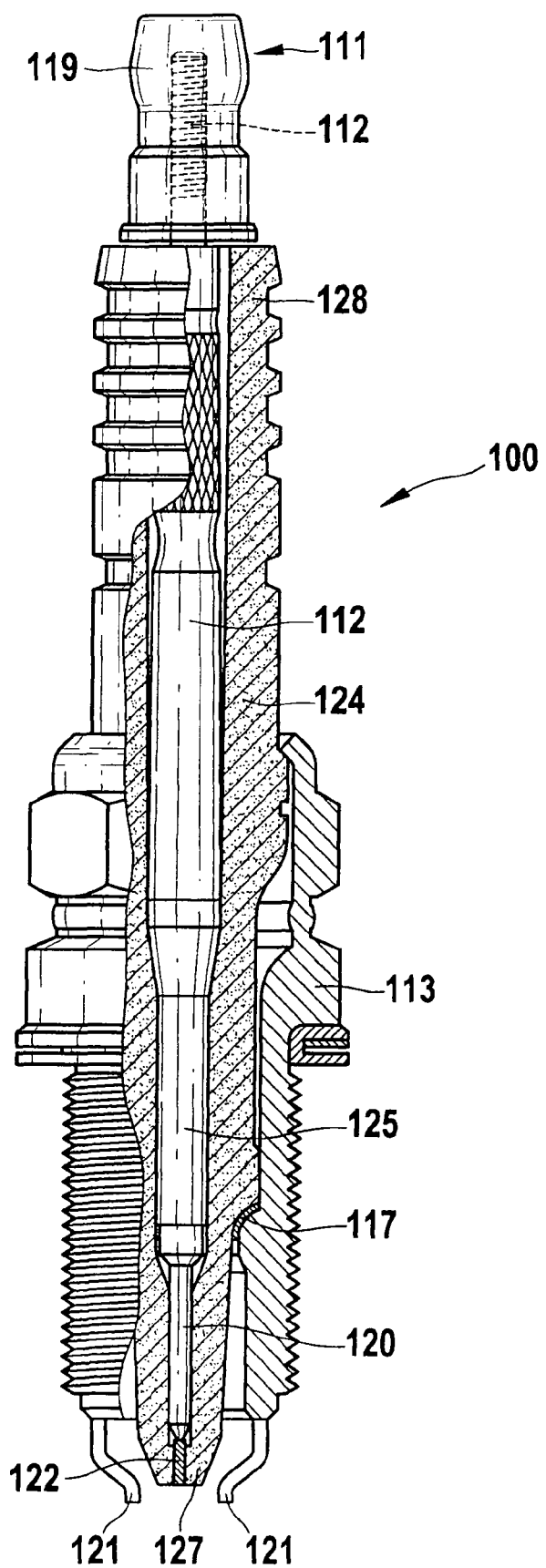
FIG. 3 shows a longitudinal section through a sensor on the basis of components of a spark plug according to a third exemplary embodiment.

FIG. 3 shows a third specific embodiment of the present sensor. This sensor is designed in the form of a spark plug. Spark plug 100 includes a tubular metallic housing 113, in which a ceramic insulator 124 is situated. On its combustion chamber side 127, insulator 124 encloses a central electrode 122, electrically insulating it against housing 113. It contains a contact pin 120, which is used for transferring the voltage to central electrode 122 and, on its connector-side end 128, a connecting arrangement 111. Connecting arrangement 111 ensures electrical contacting of central electrode 122 to an external voltage supply (not depicted). Essentially it includes a connecting bolt 112, which, on its connector-side end, is provided with a thread and a connecting nut 119. A burn-off resistor 125, which is made of electrically conductive glass and provides both mechanical anchoring of the spark plug components situated in insulator 124 and a gas-tight barrier against the combustion pressure, is situated between connecting arrangement 111 and contact pin 120. An internal sealing seat 117, which seals the inside of spark plug 100 against the combustion chamber, is situated between insulator 124 and housing 113.

Up to four ground electrodes 121 are welded to housing 113. A high voltage is applied between these electrodes and central electrode 122. The particulate concentration is then determined as with the sensors depicted and described in FIGS. 1 and 2.

Figure 4:
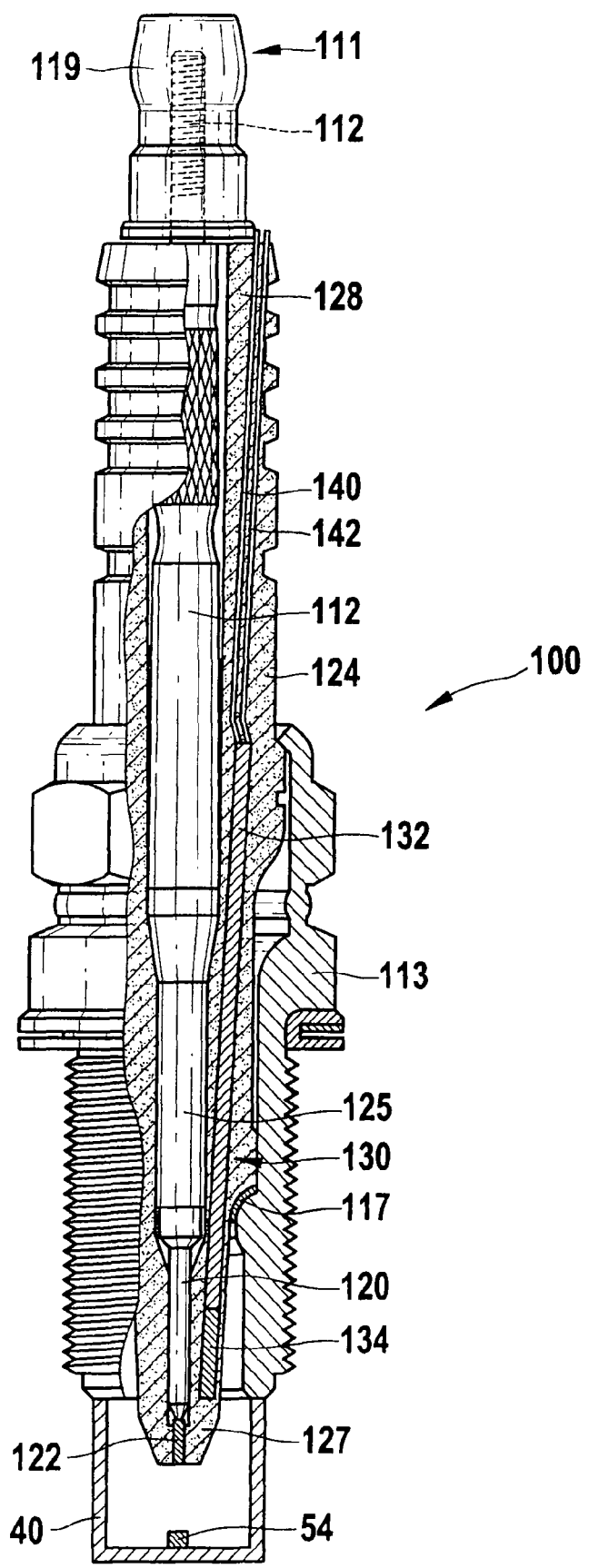
FIG. 4 shows a longitudinal section through a sensor on the basis of components of a spark plug according to a fourth exemplary embodiment.

FIG. 4 shows a further specific embodiment of a sensor designed as a spark plug. The same reference symbols denote the same components as in FIG. 3.

This sensor additionally has a heating element 130 for heating central electrode 122 in particular, in order to free it from the depositing soot. Heating element 130 is integrated into the ceramic of insulator 124 and includes a heating area 134 and a lead area 132. Heating element 130 is electrically contacted by two leads 140, 142. Heating element 130 may have a design similar to that of heating element 45 of FIGS. 1 and 2.

Furthermore, the sensor according to FIG. 4 has, instead of ground electrodes 121, a metallic protecting tube 40, which has a design comparable to that of the protecting tubes depicted in FIGS. 1 and 2 and may be a metal lamina 54 as a catch basket for electrical sparkovers. Metallic protecting tube 40 and metal laminas 54 work as a counterelectrode to central electrode 122.

Figure 5:
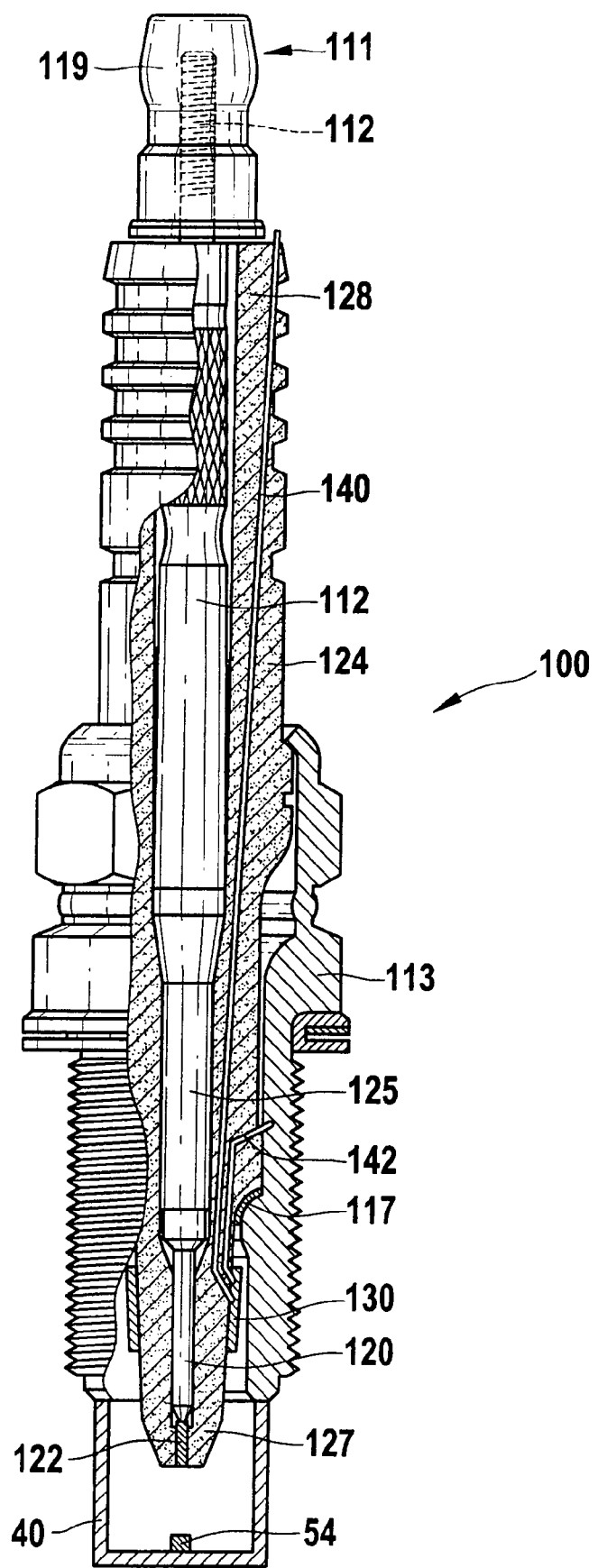
FIG. 5 shows a longitudinal section through a sensor on the basis of components of a spark plug according to a fifth exemplary embodiment.

FIG. 5 shows a variant of the sensor depicted in FIG. 4, the same reference numerals being used for the same components as in FIGS. 3 and 4.

In this case heating element 130 surrounds, which may be cylindrically, combustion chamber-side area 127 of the ceramic of the insulator and is used for heating electrodes 121, 122. Heating element 130 is applied to the outer surface of combustion chamber-side area 127 of insulator 124 by pad pressure or transfer pressure. While one of leads 142 is in contact with housing 113 and is thus grounded, additional lead 140 exits the ceramic of insulator 124 at its connector-side end 128.

What is claimed is:

1. A sensor for determining a concentration of particulates in a gas mixture, comprising:
    a ceramic sensor body surrounded by a metallic housing and having a first measuring electrode and a second measuring electrode, wherein the first measuring electrode is coupled to the metallic housing of the sensor, wherein the ceramic sensor body is surrounded by and spaced from a protecting tube, and wherein the first measuring electrode is formed by the protecting tube.

2. The sensor of claim 1, wherein the second measuring electrode is at least largely integrated into the ceramic sensor body.

3. The sensor of claim 1, wherein the ceramic sensor body contains at least one of zirconium dioxide, aluminum oxide, and alkaline earth oxide.

4. The sensor of claim 1, wherein a high voltage is applicable to the measuring electrodes so that an electrical discharge occurs between the measuring electrodes.

5. The sensor of claim 1, further comprising:
    an analyzer device to ascertain a number of discharges per unit of time and to output it as a measure for the particulate concentration in the gas mixture.

6. The sensor of claim 1, wherein the ceramic sensor body includes a depression where a heating element is introduced.

7. The sensor of claim 1, wherein the ceramic sensor body includes a rotationally symmetric design.

8. The sensor of claim 1, wherein the ceramic sensor body includes a reference electrode.

9. The sensor of claim 1, wherein the ceramic sensor body includes a third measuring electrode.

10. The sensor of claim 1, wherein the sensor is operable as a lambda sensor.

11. The sensor of claim 1, wherein the sensor is operable as a spark plug.

12. The sensor of claim 1, wherein a heating element is provided.

13. A method for determining particulates in a gas mixture, the method comprising:
    exposing a sensor having a first and a second measuring electrode to a gas mixture, the sensor including a ceramic sensor body; and
    applying a high voltage to the first measuring electrode;
    wherein an electrode coupled thereto is used as the second measuring electrode, wherein the ceramic sensor body is surrounded by and spaced from a protecting tube, and wherein the second measuring electrode is formed by the protecting tube.

14. The method of claim 13, wherein the sensor is for determining a concentration of particulates in a gas mixture, and wherein the ceramic sensor body is surrounded by a metallic housing and having the first measuring electrode and the second measuring electrode, wherein the first measuring electrode is coupled to the metallic housing of the sensor or the metallic housing of the sensor is arranged as the first measuring electrode.

15. The method of claim 13, wherein a high voltage is applied between the first and the second measuring electrodes in a first time period, and a voltage is determined between another measuring electrode and an additionally provided reference electrode in a second time period.

16. A sensor for determining a concentration of particulates in a gas mixture, comprising:
    a ceramic sensor body surrounded by a metallic housing and having a first measuring electrode and a second measuring electrode, wherein the first measuring electrode is mounted on the metallic housing of the sensor, wherein the ceramic sensor body additionally includes a reference electrode, and wherein the first measuring electrode is formed by the protecting tube.

17. The sensor of claim 16, wherein the second measuring electrode is at least largely integrated into the ceramic sensor body.

18. The sensor of claim 16, wherein the ceramic sensor body contains at least one of zirconium dioxide, aluminum oxide, and alkaline earth oxide.

19. The sensor of claim 16, wherein a high voltage is applicable to the measuring electrodes so that an electrical discharge occurs between the measuring electrodes.

20. The sensor of claim 19, further comprising:
    an analyzer device to ascertain a number of discharges per unit of time and to output it as a measure for the particulate concentration in the gas mixture.

21. The sensor of claim 16, wherein the ceramic sensor body includes a depression where a heating element is introduced.

22. The sensor of claim 16, wherein the ceramic sensor body includes a rotationally symmetric design.

23. The sensor of claim 16, wherein the ceramic sensor body includes a third measuring electrode.

24. The sensor of claim 16, wherein the sensor constitutes a lambda sensor.

25. A method for determining particulates in a gas mixture, the method comprising:

exposing a sensor having a first and a second measuring electrode to a gas mixture; and
applying a high voltage to the first measuring electrode;
wherein an electrode mounted on the metallic housing is used as the second measuring electrode, wherein the sensor is surrounded by and spaced from a protecting tube, wherein the second measuring electrode is formed by the protecting tube, wherein a high voltage is applied between the first and the second measuring electrodes in a first time period, and a voltage is determined between another measuring electrode and an additionally provided reference electrode in a second time period.

26. The method of claim 25, wherein the sensor is for determining a concentration of particulates in a gas mixture, and wherein a ceramic sensor body is surrounded by the metallic housing and having the first measuring electrode and the second measuring electrode, wherein the first measuring electrode is coupled to the metallic housing of the sensor or the metallic housing of the sensor is arranged as the first measuring electrode.

* * * * *